(12) United States Patent
Okumura

(10) Patent No.: US 7,742,155 B2
(45) Date of Patent: Jun. 22, 2010

(54) DIFFUSION MATERIAL, DIFFUSION MATERIAL EVALUATING METHOD, BLENDING METHOD FOR FINE PARTICLES IN THE DIFFUSION MATERIAL, AND PRODUCTION METHOD FOR THE DIFFUSION MATERIAL

(75) Inventor: Takamitsu Okumura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 290 days.

(21) Appl. No.: 11/910,323

(22) PCT Filed: Mar. 30, 2006

(86) PCT No.: PCT/JP2006/306700

§ 371 (c)(1),
(2), (4) Date: Oct. 1, 2007

(87) PCT Pub. No.: WO2006/106843

PCT Pub. Date: Oct. 12, 2006

(65) Prior Publication Data

US 2009/0115998 A1 May 7, 2009

(30) Foreign Application Priority Data

Mar. 31, 2005 (JP) ............................. 2005-102556

(51) Int. Cl.
*G01N 21/27* (2006.01)
*G01M 11/00* (2006.01)
*G02B 5/02* (2006.01)
(52) U.S. Cl. ........................................ 356/73; 359/599
(58) Field of Classification Search ........................ None
See application file for complete search history.

(56) References Cited

U.S. PATENT DOCUMENTS

| 6,217,184 | B1 | 4/2001 | Koike et al. |
| 6,238,827 | B1 | 5/2001 | Nakazawa et al. |
| 6,907,177 | B2 | 6/2005 | Iwasaki et al. |

FOREIGN PATENT DOCUMENTS

| JP | 11-153963 A | 6/1999 |
| JP | 2000-009916 A | 1/2000 |
| JP | 2004-101763 A | 4/2004 |
| JP | 2005-31379 A | 2/2005 |

OTHER PUBLICATIONS

IPER dated Oct. 11, 2007.
Japanese Patent Office International Search Report dated Jun. 27, 2006.

*Primary Examiner*—F. L Evans
(74) *Attorney, Agent, or Firm*—Sughrue Mion, PLLC

(57) ABSTRACT

A diffusion material includes a prescribed scattering $S(\lambda)$ of respective fine particles that are determined by Mie theory for all plural kinds of fine particles at a wavelength $\lambda$ of an incident light. The diffusion material includes plural kinds of fine particles having different refractive indices, dispersed into a matrix. Each particle providing light intensity attenuating rate $C(\lambda)$ in the diffusion material, and chromaticity variations $\Delta x$ and $\Delta y$ of the incident light. The diffusion power of the diffusion material by using determined chromaticity variations $\Delta x$ and $\Delta y$; the diffusion material that is evaluated by this evaluation method and can emit illumination light free from wavelength unevenness. The diffusion material includes a blending fine particles to provide the prescribed diffusion and uniform illumination.

6 Claims, 4 Drawing Sheets

DIFFUSION MATERIAL, DIFFUSION MATERIAL EVALUATING METHOD, BLENDING METHOD FOR FINE PARTICLES IN THE DIFFUSION MATERIAL, AND PRODUCTION METHOD FOR THE DIFFUSION MATERIAL

TECHNICAL FIELD

The present invention relates to a technical field of a diffusion material into which a material having a refractive index different from that of a matrix is introduced, and specifically, to a technical field of a diffusion material for, for example, a diffusion sheet or diffusion panel for use in, for example, the lighting unit (backlight unit) of a liquid crystal display device or a diffusion material for use, for example, in a member (screen) for forming an image with an image signal from a projector or in any one of various lighting units, and a method of evaluating the diffusion material, a method of designing the diffusion material, that is, a method of blending fine particles, and a method of producing the diffusion material. More specifically, the present invention relates to a method of evaluating a diffusion material that diffuses incident light for diffusion power, a diffusion material which is evaluated by the evaluating method and which can emit illumination light free from wavelength unevenness, and a method of blending fine particles having different refractive indices in a matrix in the diffusion material for designing and producing the diffusion material and a method of producing the diffusion material.

BACKGROUND ART

A material for diffusing light has recently found use in a variety of fields. For example, in the case of interior illumination, the quantity of emitted light is uniformized by passing the light through a diffusion panel instead of directly illuminating a room with a fluorescent lamp. In addition, a direct type backlight unit to be used as the backlight unit of a large liquid crystal television set is also converted into a uniform planar light source by placing a diffusion panel on a fluorescent tube to alleviate brightness unevenness.

A light diffusion material as exemplified by such diffusion panel produces a diffusion effect by adding materials such as fine particles having different refractive indices to a matrix to induce a light scattering phenomenon.

However, the light scattering phenomenon has wavelength dependency as typified by the blue sky, so a light scattering material involves the following problem: the wavelength dependency of a white light source changes, and white light is observed to be color unevenness.

JP 11-153963 A (Cited Document 1) proposes a diffusion material for improving the uniformity of a color tone to solve the problem. The diffusion material disclosed in Cited Document 1 is a light scattering light guide the inside of which is provided with scattering power by dispersing, in a medium having a predetermined refractive index (a matrix or a matrix), scatterers such as spherical fine particles each having a refractive index different from that of the matrix. The diffusion material is used in a light source device which: is provided with light supplying means for supplying visible light including a long wavelength region and a short wavelength region from a side end face portion of the light scattering light guide; and causes incident light to outgo from an outgoing surface formed in at least a side portion of the light scattering light guide. In addition, Cited Document 1 discloses that evaluation for the scattering power imparted to the light scattering light guide can be performed by using scattering efficiency $Q(\lambda)$ ($\lambda$: wavelength) determined from the theory of Mie scattering. That is, the scattering power imparted to the light scattering light guide of Cited Document 1 is as follows: a relationship between scattering efficiency $Q(R)$ in a long wavelength region (long wavelength visible region typified by a red color) and scattering efficiency $Q(B)$ in a short wavelength region (short wavelength visible region typified by a blue color) is balanced so that the color temperature of outgoing light from the outgoing surface at a position close to an incident side end face portion and the color temperature of the light at a position distant from the position are substantially equal to each other.

In addition, Cited Document 1 further discloses that a control ratio k for balancing the scattering efficiency $Q(\lambda)$ represented by a ratio between the scattering efficiency $Q(B)$ in a short wavelength region and the scattering efficiency $Q(R)$ in a long wavelength region is preferably adjusted to satisfy the following range:

$$k = Q(B)/Q(R)$$

$$0.75 \leq k \leq 1.25$$

where B=435 (nm) (blue color) and R=615 (nm) (red color).

In addition, the document discloses that the shape of the light scattering light guide is preferably a plate shape, a wedge shape (which tends to be thinner as it is more distant from a side end face portion), or a rod shape.

As a result, in Cited Document 1, a problem concerning color unevenness occurring in a light source device using a light scattering light guide is solved, the nonuniformity of the color tone of outgoing light depending on whether the light is distant from or close to a light supply end is alleviated, and the uniformity of a color tone, for example, in the backlighting of any one of various displays such as a liquid crystal display or in any one of the other various lighting units can be easily improved.

Patent Document 1: JP 11-153963 A

DISCLOSURE OF THE INVENTION

Problems to be Solved by the Invention

However, the scattering efficiency $Q(\lambda)$ determined from the theory of Mie scattering applied in Cited Document 1 is a parameter uniquely determined in the case where a fine particle as a scatterer is a true spherical fine particle having a single particle diameter, and the efficiency is a theoretical value theoretically determined when the fine particle is assumed to have a single particle diameter. In addition, even in Cited Document 1, the scattering efficiency is calculated on the assumption that a scatterer described in an example of the document is a true spherical fine particle.

In actuality, however, in general, there are no particles each of which is free from particle size distribution. In addition, even when one attempts to uniformize the particle sizes of fine particles to be used as scatterers to be dispersed in a matrix, it is extremely difficult to produce fine particles each having a single particle diameter, and the particle size distribution is necessarily present.

Accordingly, Cited Document 1, which defines a scatterer as a fine particle having a single particle diameter, involves the following problem: the scattering efficiency $Q(\lambda)$ cannot be calculated because a fine particle to be actually used as a scatterer has particle size distribution. That is, the following problem arises: the scattering efficiency defined in Cited Document 1 cannot be accurately determined in an actual light scattering light guide using an actual fine particle having a particle size distribution as a scatterer, and the actual light scattering light guide cannot be accurately evaluated for scattering power on the basis of the scattering efficiency disclosed in Cited Document 1. Moreover, when a fine particle having multiple particle diameters is used as a scatterer, the following problem arises: a light scattering light guide cannot be accurately evaluated for scattering power on the basis of the scattering efficiency disclosed in Cited Document 1.

In addition, Cited Document 1 has no disclosure concerning the allowable range of a color temperature used as an indication of color unevenness, so the following problem arises: a correlation between the allowable range and the range of the control ratio k as a ratio between scattering efficiency in a short wavelength region and scattering efficiency in a long wavelength region cannot be known. Accordingly, the following problem arises: even when a scatterer is adjusted so that the control ratio k falls within the range of Cited Document 1, a color tone becomes nonuniform, and a human being visually feels color unevenness.

It should be noted that the light source device described in Cited Document 1 is basically assumed to be used in a side light type backlight, and involves the following problem: the angle distribution of outgoing light that is of greater concern than wavelength unevenness from position to position cannot be solved in, for example, a direct type backlight (for use in a diffusion panel) or a bridge type backlight.

In addition, as described above, the adjustment of the control ratio k between the scattering efficiency Q(B) in a short wavelength region and the scattering efficiency Q(R) in a long wavelength region in Cited Document 1 refers to the selection of one particle diameter with which the scattering efficiency $Q(\lambda)$ does not have wavelength dependency. However, commercially available fine particles each have a particle size distribution, and a larger difference in refractive index between a matrix and each of the fine particles makes the wavelength dependency of scattering more remarkable at a certain particle diameter, so it is difficult to select a particle diameter appropriately.

An object of the present invention is to solve the above-mentioned problems of the prior art, and to provide: a method of evaluating a diffusion material by which a diffusion material can be accurately evaluated for scattering power, and, furthermore, by which, even when a fine particle having a particle size distribution is added, or even when a fine particle having large wavelength dependency is used, a diffusion material can be accurately evaluated for scattering power by accurately judging whether a chromaticity variation of emitted light outgoing from the diffusion material with respect to incident light entering the diffusion material falls within a certain range; a diffusion material which is evaluated by the evaluating method and which can emit illumination light formed of white light free from wavelength unevenness; and a method of blending fine particles in a diffusion material and a method of producing a diffusion material by each of which the blending amounts of fine particles in a matrix are designed so that a chromaticity variation of the emitted light outgoing from a diffusion material with respect to the incident light entering the diffusion material falls within a predetermined range, and a diffusion material capable of emitting illumination light free from wavelength unevenness can be obtained.

In addition, another object of the present invention is to provide: a diffusion material with which, even when a fine particle having large wavelength dependency is used, the color unevenness of emitted light caused by the large dependency can be reduced, and high efficiency for light utilization can be realized simultaneously with the emission of white light free from wavelength unevenness, and hence multiple light sources having different wavelengths such as LED's can be efficiently subjected to color mixing to provide white light, and, furthermore, even when a light source has wavelength dependency, the color tone of emitted light due to the wavelength dependency can be reduced; a method of evaluating the diffusion material; a method of blending fine particles in the diffusion material; and a method of producing the diffusion material as well as to achieve the above object.

Means to Solve the Problems

The inventors of the present invention have made intensive studies with a view to solving the above-mentioned problems. As a result, the inventors have found that, when a particle has a particle size distribution, or when particles each having multiple particle diameters are dispersed, evaluation should be performed by using a cross-sectional area of scattering (total energy scattered per unit time) in the entire system as an adjustment parameter. In addition, the inventor has found that an allowable range where a human being does not visually feel any wavelength unevenness should be clearly described as a color difference range, and a correlation between the range and a control ratio for a cross-sectional area of scattering should be clearly described. Further, the inventors have found that, when the application of a light source device to not only a side light (tandem) type backlight but also a direct type backlight (for use in a diffusion panel), a bridge type backlight, or the like is taken into consideration, the angle distribution of emitted light is of greater concern than wavelength unevenness from position to position in the direct or bridge type backlight. Thus, the inventor has completed the present invention.

A first aspect of the present invention provides a method of evaluating a diffusion material in which multiple kinds of fine particles each kind of which have a refractive index different from a refractive index of a matrix are dispersed in the matrix by evaluating diffusion power of the diffusion material, comprising the steps of:

determining a total cross-sectional area of scattering $S_{total}(\lambda)$ in the diffusion material as a total of cross-sectional areas of scattering $S(\lambda)$ of respective fine particles that are determined by Mie theory for all of the multiple kinds of fine particles dispersed in the matrix at a wavelength $\lambda$ of incident light entering the diffusion material;

determining a light intensity attenuating rate $C(\lambda)$ in the diffusion material from the total cross-sectional area of scattering $S_{total}(\lambda)$ in the diffusion material;

determining chromaticity variations $\Delta x$ and $\Delta y$ of emitted light outgoing from the diffusion material with respect to the incident light entering the diffusion material by using the light intensity attenuating rate $C(\lambda)$ in the diffusion material; and evaluating the diffusion power of the diffusion material by using the thus determined chromaticity variations $\Delta x$ and $\Delta y$ of the emitted light with respect to the incident light.

It is preferable to determine a relative refractive index $m_i$ between an i-th kind (i=2, ..., n) of fine particles and the matrix from the following expression (1); and determine the total cross-sectional area of scattering $S_{total}(\lambda)$ in the diffusion material from the following expressions (2-1) and (2) by using the relative refractive index $m_i$ thus determined. In the following expressions (1), (2-1), and (2), $n_m(\lambda)$ denotes the refractive index of the matrix, $n_{pi}(\lambda)$ denotes a refractive index of the i-th kind of fine particles, $A_i$ denotes a blending ratio at which the i-th kind of fine particles are blended, $r_i$ denotes a particle size of the i-th kind of fine particles, $F(r_i)$ denotes a particle size distribution function of the multiple kinds of fine particles, $m_i$ denotes the relative refractive index between the i-th kind of fine particles and the matrix, $S_i(m_i, \lambda)$ denotes cross-sectional areas of scattering of the i-th kind of fine particles, L denotes a thickness of the diffusion material, and N denotes a number density of fine particles in the diffusion material, for example N [particles/m³].

$$m_i = n_{pi}(\lambda)/n_m(\lambda) \qquad (1)$$

$$S_r(\lambda) = N \sum_{i=1}^{\infty} S_i(m, \lambda) F(r_i) \qquad (2\text{-}1)$$

$$S_{total}(\lambda) = \sum_{i=1}^{n} S_i(\lambda) N A_i \sum_{i=1}^{n} A_i = 1 \qquad (2)$$

The particle size distribution function F(r) of the fine particles is preferably represented by the following expression (8):

$$F(r) = \frac{1}{\sqrt{2\pi Npq}} \exp\left[-\frac{(r-Np)^2}{2Npq}\right], q = 1-p \qquad (8)$$

where $N_0$ represents a total number of particles, F(r) denotes the number of particles having a particle diameter of r, p denotes a probability that the particles having the particle diameter of r is present, Np denotes an average particle diameter, and Npq denotes a variance.

It is preferable to determine a relative refractive index $m_i$ between an i-th kind (i=2, ..., n) of fine particles and the matrix from the following expression (1), and determine the total cross-sectional area of scattering $S_{total}(\lambda)$ in the diffusion material from the following expressions (2-2) and (2) by using the relative refractive index $m_i$ thus determined. In the expressions (1), (2-2), and (2), $n_m(\lambda)$ denotes the refractive index of the matrix, $n_{pi}(\lambda)$ denotes a refractive index of the i-th kind of fine particles, $A_i$ denotes a blending ratio at which the i-th kind of fine particles are blended, δ denotes a particle size of each of the fine particles, $f_i(\delta)$ denotes a particle size distribution function of the i-th kind of fine particles, $m_i$ denotes the relative refractive index between the i-th kind of fine particles and the matrix, $S_i(\delta, m_i, \lambda)$ denotes cross-sectional areas of scattering of the i-th kind of fine particles, L denotes a thickness of the diffusion material, and N denotes a number density of fine particles in the diffusion material, for example N [particles/m³].

$$m_i = n_{pi}(\lambda)/n_m(\lambda) \qquad (1)$$

$$S_i(\lambda) = N \int_0^{\infty} S_i(\delta, mi, \lambda) f_i(\delta) d\delta \qquad (2\text{-}2)$$

$$S_{total}(\lambda) = \sum_{i=1}^{n} S_i(\lambda) N A_i \sum_{i=1}^{n} A_i = 1 \qquad (2)$$

It is preferable that the particle size distribution of the fine particles forms a normal distribution and that the particle size distribution function $f_i(\delta)$ is represented by the following expression (8-1):

$$f_i(\delta) = \frac{1}{\sigma_i \sqrt{2\Pi}} \exp\left[-\frac{1}{2}\left(\frac{\delta - \mu_i}{\sigma_i}\right)^2\right] \qquad (8\text{-}1)$$

where $\mu_i$ denotes an average particle diameter of the i-th kind of fine particles, and $\sigma_i$ denotes a standard deviation of thereof.

It is preferable to determine the light intensity attenuating rate $C(\lambda)$ in the diffusion material from the following expression (3) by using the total cross-sectional area of scattering $S_{total}(\lambda)$ in the diffusion material;

determine an intensity $P'(\lambda)$ of the emitted light outgoing from the diffusion material from the following expression (4) by using the thus determined light intensity attenuating rate $C(\lambda)$ and an intensity $P(\lambda)$ of the incident light entering the diffusion material;

determine chromaticities x and y of the incident light, and chromaticities x' and y' of the emitted light from the following expressions (5) and (6) by using the thus determined intensity $P'(\lambda)$ of the emitted light and the intensity $P(\lambda)$ of the incident light; and determine the chromaticity variations Δx and Δy of the emitted light with respect to the incident light from the following expression (7) by using the thus determined chromaticities x and y of the incident light, and the thus determined chromaticities x' and y' of the emitted light:

$$C(\lambda) = \exp[-S_{total}(\lambda) \cdot L] \qquad (3)$$

$$P'(\lambda) = C(\lambda) P(\lambda) \qquad (4)$$

$$\begin{cases} X' = \int_\lambda P'(\lambda) \bar{x}(\lambda) d\lambda \\ Y' = \int_\lambda P'(\lambda) \bar{y}(\lambda) d\lambda \\ Z' = \int_\lambda P'(\lambda) \bar{z}(\lambda) d\lambda \end{cases} \begin{cases} X = \int_\lambda P(\lambda) \bar{x}(\lambda) d\lambda \\ Y = \int_\lambda P(\lambda) \bar{y}(\lambda) d\lambda \\ Z = \int_\lambda P(\lambda) \bar{z}(\lambda) d\lambda \end{cases} \qquad (5)$$

where X', Y', and Z' denote tristimulus values of the emitted light, X, Y, and Z denote tristimulus values of the incident light, and xbar, ybar, and zbar denote color matching functions.

$$\begin{cases} x' = \frac{X'}{X'+Y'+Z'} \\ y' = \frac{Y'}{X'+Y'+Z'} \end{cases} \begin{cases} x = \frac{X}{X+Y+Z} \\ y = \frac{Y}{X+Y+Z} \end{cases} \qquad (6)$$

$$\Delta x = x' - x \qquad (7)$$
$$\Delta x = y' - y$$

The diffusion power of the diffusion material is preferably evaluated depending on whether the chromaticity variations Δx and Δy of the emitted light with respect to the incident light satisfy the following expression (9), respectively:

$$-0.03 \leq \Delta x \leq 0.03$$
$$-0.03 \leq \Delta y \leq 0.03 \qquad (9).$$

A second aspect of the present invention provides a diffusion material evaluated by the method of evaluating the diffusion material according to the first aspect of the present invention to have the diffusion power such that the chromaticity variations $\Delta x$ and $\Delta y$ of the emitted light with respect to the incident light satisfy the following expression (9), respectively:

$$-0.03 \leq \Delta x \leq 0.03$$

$$-0.03 \leq \Delta y \leq 0.03 \qquad (9).$$

A third aspect of the present invention provides a method of blending multiple kinds of fine particles each kind of which have a refractive index different from a refractive index of a matrix in a diffusion material in which the multiple kinds of fine particles are dispersed in the matrix in order to obtain desired diffusion power, comprising the steps of:

determining a light intensity attenuating rate $C(\lambda)$ in the diffusion material so that chromaticity variations $\Delta x$ and $\Delta y$ of emitted light outgoing from the diffusion material with respect to incident light entering the diffusion material satisfy the following expression (9), respectively, determining a total cross-sectional area of scattering $S_{total}(\lambda)$ in the diffusion material at a wavelength $\lambda$ of the incident light entering the diffusion material so that a condition for the light intensity attenuating rate $C(\lambda)$ in the diffusion material thus determined is satisfied;

determining blending amounts of the multiple kinds of fine particles dispersed in the matrix so that the total cross-sectional area of scattering $S_{total}(\lambda)$ in the diffusion material thus determined is determined as a total of cross-sectional areas of scattering $S(\lambda)$ of respective fine particles that are determined by Mie theory for all of the multiple kinds of fine particles dispersed in the matrix; and blending the multiple kinds of fine particles in accordance with the thus determined blending amounts.

$$-0.03 \leq \Delta x \leq 0.03$$

$$-0.03 \leq \Delta y \leq 0.03 \qquad (9).$$

It is preferable to determine chromaticities x and y of the incident light, and chromaticities x' and y' of the emitted light by using the following expression (7) from the chromaticity variations $\Delta x$ and $\Delta y$ of the emitted light with respect to the incident light;

determine an intensity $P'(\lambda)$ of the emitted light and an intensity $P(\lambda)$ of the incident light by using the following expressions (5) and (6) from the chromaticities x and y of the incident light, and the chromaticities x' and y' of the emitted light thus determined;

determine the light intensity attenuating rate $C(\lambda)$ in the diffusion material by using the following expression (4) from the intensity $P'(\lambda)$ of the emitted light and the intensity $P(\lambda)$ of the incident light thus determined;

determine the total cross-sectional area of scattering $S_{total}(\lambda)$ in the diffusion material by using the following expression (3) from the light intensity attenuating rate $C(\lambda)$ in the diffusion material thus determined; and determine a range of a ratio $S_{total}(B)/S_{total}(R)$ of the total cross-sectional area of scattering in blue light to the total cross-sectional area of scattering in red light represented by the following expression (10) when three major wavelengths of the incident light entering the diffusion material are represented by B (blue light), G (green light), and R (red light).

$$C(\lambda) = \exp[-S_{total}(\lambda) \cdot L] \qquad (3)$$

$$P'(\lambda) = C(\lambda) P(\lambda) \qquad (4)$$

-continued $$\begin{cases} X' = \int_\lambda P'(\lambda)\bar{x}(\lambda)d\lambda \\ Y' = \int_\lambda P'(\lambda)\bar{y}(\lambda)d\lambda \\ Z' = \int_\lambda P'(\lambda)\bar{z}(\lambda)d\lambda \end{cases} \begin{cases} X = \int_\lambda P(\lambda)\bar{x}(\lambda)d\lambda \\ Y = \int_\lambda P(\lambda)\bar{y}(\lambda)d\lambda \\ Z = \int_\lambda P(\lambda)\bar{z}(\lambda)d\lambda \end{cases} \qquad (5)$$

where X', Y', and Z' denote tristimulus values of the outgoing light, X, Y, and Z denote tristimulus values of the incident light, and xbar, ybar, and zbar denote color matching functions:

$$\begin{cases} x' = \dfrac{X'}{X'+Y'+Z'} \\ y' = \dfrac{Y'}{X'+Y'+Z'} \end{cases} \begin{cases} x = \dfrac{X}{X+Y+Z} \\ y = \dfrac{Y}{X+Y+Z} \end{cases} \qquad (6)$$

$$\Delta x = x' - x \qquad (7)$$

$$\Delta x = y' - y$$

$$K\min \leq S_{total}(B)/S_{total}(R) \leq K\max. \qquad (10)$$

It is preferable to determine a relative refractive index $m_i$ between an i-th kind (i=2, ..., n) of fine particles and the matrix from the following expression (1) when a particle size distribution function $F(r_i)$ of each of the multiple kinds of fine particles is represented by the following expression (8); and determine a blending ratio $A_i$ at which the i-th kind of fine particles are blended from the following expressions (2-1) and (2) by using the relative refractive index $m_i$ thus determined and the range of the total cross-sectional area of scattering $S_{total}(B)$ and $S_{total}(R)$ in the diffusion material. In the expressions (1), (2-1), and (2), $n_m(\lambda)$ denotes the refractive index of the matrix, $n_{pi}(\lambda)$ denotes a refractive index of the i-th kind of fine particles, $r_i$ denotes a particle size of the i-th kind of fine particles, $m_i$ denotes the relative refractive index between the i-th kind of fine particles and the matrix, $S_i(m_i, \lambda)$ denotes cross-sectional areas of scattering of the i-th kind of fine particles, L denotes a thickness of the diffusion material, and N denotes a number density of fine particles in the diffusion material, for example N [particles/m³].

$$m_i = n_{pi}(\lambda)/n_m(\lambda) \qquad (1)$$

$$S_r(\lambda) = N \sum_{i=1}^{\infty} S_i(m,\lambda) F(r_i) \qquad (2\text{-}1)$$

$$S_{total}(\lambda) = \sum_{i=1}^{n} S_i(\lambda) N A_i \sum_{i=1}^{n} A_i = 1 \qquad (2)$$

$$F(r) = \dfrac{1}{\sqrt{2\pi Npq}} \exp\left[-\dfrac{(r-Np)^2}{2Npq}\right], q = 1-p \qquad (8)$$

where $N_0$ denotes a total number of particles, F(r) denotes the number of particles having a particle diameter of r, p denotes a probability that the particles having the particle diameter of r is present, Np denotes an average particle diameter, and Npq denotes a variance.

It is preferable to determine a relative refractive index $m_i$ between an i-th kind (i=2, ..., n) of fine particles and the matrix from the following expression (1) when a particle size distribution function $f_i(\delta)$ of the i-th kind of fine particles forms a normal distribution, and is represented by the following expression (8-1); and determine a blending ratio $A_i$ at which the i-th kind of fine particles are blended from the following expressions (2-2) and (2) by using the relative refractive index $m_i$ thus determined and the range of the total cross-sectional area of scattering $S_{total}(B)$ and $S_{total}(R)$ in the diffusion material. In the expressions (1), (2-2) and (2), $n_m(\lambda)$ denotes the refractive index of the matrix, $n_{pi}(\lambda)$ denotes a refractive index of the i-th kind of fine particles, $\delta$ denotes a particle size of each of the fine particles, $m_i$ denotes the relative refractive index between the i-th kind of fine particles and the matrix, $S_i(\delta, m_i, \lambda)$ denotes cross-sectional areas of scattering of the i-th kind of fine particles, L denotes a thickness of the diffusion material, and N denotes a number density of fine particles in the diffusion material, for example, N [particles/m³].

$$m_i = n_{pi}(\lambda)/n_m(\lambda) \tag{1}$$

$$S_i(\lambda) = N \int_0^\infty S_i(\delta, mi, \lambda) f_i(\delta) d\delta \tag{2-2}$$

$$S_{total}(\lambda) = \sum_{i=1}^{n} S_i(\lambda) N A_i \sum_{i=1}^{n} A_i = 1 \tag{2}$$

$$f_i(\delta) = \frac{1}{\sigma_i \sqrt{2\Pi}} \exp\left[-\frac{1}{2}\left(\frac{\delta - \mu_i}{\sigma_i}\right)^2\right] \tag{8-1}$$

where $\mu_i$ denotes an average particle diameter of the i-th kind of fine particles, and $\sigma_i$ denotes a standard deviation of thereof.

A fourth aspect of the present invention provides a method of producing a diffusion material comprising the steps of melting, mixing, and dispersing the multiple kinds of fine particles blended by the method of blending the fine particles in the diffusion material according to the third aspect of the present invention.

It should be noted that the term "dispersion of multiple kinds of fine particles each having a refractive index different from that of the matrix of a diffusion material in the diffusion material" as used in the present invention includes all cases except the case where a fine particle having a single particle diameter is dispersed in the matrix of the diffusion material. For example, the case where fine particles made of the same material, having the same refractive index, and different from each other only in particle size or particle size distribution, or merely fine particles each having a particle size distribution are dispersed in the matrix is permitted. Of course, fine particles different from each other in one or both of material and refractive index may be dispersed. Further, when the fine particles to be dispersed in the matrix are different from each other in one or both of material and refractive index, the fine particles may be fine particles each having a single particle diameter, or may be fine particles each having a particle size distribution.

It should be noted that, when multiple kinds of fine particles to be used in the present invention are regarded as multiple kinds of fine particles because of their predetermined particle size distributions, it is sufficient to regard the respective particle sizes to be distributed as one kind in each of the above aspects; in the present invention, a total cross-sectional area of scattering $S_{total}(\lambda)$ in a diffusion material may be determined by regarding the fine particles as fine particles of one kind each having the above-mentioned predetermined particle size distribution and calculating each of the above expressions with i=n=1 (one kind) in each of the above aspects, or the total cross-sectional area of scattering can be determined as described below.

In this case, the total cross-sectional area of scattering $S_{total}(\lambda)$ in the diffusion material may be determined from the following expressions (1-1) and (2-3) by using the cross-sectional area of scattering $S(\delta, m, \lambda)$ of a fine particle determined by Mie theory when the refractive index of the fine particle is represented by $n_p(\lambda)$, the particle size distribution function of the fine particle at a particle diameter $\delta$ of the fine particle is represented by $f(\delta)$, and a relative refractive index between the fine particle and the matrix is represented by m. It should be noted that, when the particle size distribution of the fine particle forms a normal distribution in this case, it is sufficient to use a distribution function represented by the following expression (8-2) as a particle size distribution function $f(r)$; when the particle size distribution of the fine particle is discrete, for example, the distribution forms a binomial distribution, it is sufficient to use the distribution function $F(r)$ represented by the above expression (8) instead of the following particle size distribution function $f(r)$.

$$m = n_p(\lambda)/n_m(\lambda) \tag{1-1}$$

$$S_{total}(\lambda) = N \int_0^\infty S(\delta, m, \lambda) f(\delta) d\delta \tag{2-3}$$

$$f(\delta) = \frac{1}{\sigma \sqrt{2\Pi}} \exp\left[-\frac{1}{2}\left(\frac{\delta - \mu}{\sigma}\right)^2\right] \tag{8-2}$$

where $\mu$ represents an average particle diameter, and $\sigma$ represents a standard deviation.

EFFECTS OF THE INVENTION

According to any one of the first to fourth aspects of the present invention, a diffusion condition taking the allowable range of a chromaticity variation in the human eye into consideration can be selected.

In addition, according to the present invention, the conditions (including a particle diameter and a concentration) under which illumination light such as white light free from wavelength unevenness is emitted can be determined while a particle size distribution possessed by a diffusion particle is taken into consideration.

Further, according to the present invention, even when a particle having large wavelength dependency is used, illumination light such as white light free from wavelength unevenness can be obtained by selecting and dispersing multiple kinds of particles so that a human being does not visually observe wavelength unevenness.

In addition, according to the present invention, even when white light is obtained by using multiple kinds of R, G, and B light sources different from each other in wavelength such as LED's, the illumination light exemplified by white light in the emitted light of which a human being does not visually observe wavelength unevenness can be obtained by selecting at least one particle and adjusting a chromaticity variation as in the case of the foregoing.

Further, according to the present invention, even when fine particles to be mixed in a diffusion material each have a particle size distribution, a chromaticity variation can be suitably adjusted by causing a total cross-sectional area of scattering to fall within the above predetermined range.

In addition, according to the present invention, there can be provided a method of designing a diffusion material by which a chromaticity variation of emitted light outgoing from the diffusion material with respect to incident light upon the diffusion material falls within a certain range, and a diffusion material produced by the designing method.

BEST MODE FOR CARRYING OUT THE INVENTION

A diffusion material, method of evaluating a diffusion material, method of blending fine particles in a diffusion material, and method of producing a diffusion material according to the present invention will be described in detail below on the basis of preferred examples shown in attached drawings.

First, the outline of a basic novel technique to be used in each of the method of evaluating a diffusion material and method of blending fine particles in a diffusion material of the present invention will be described.

Figure 1:
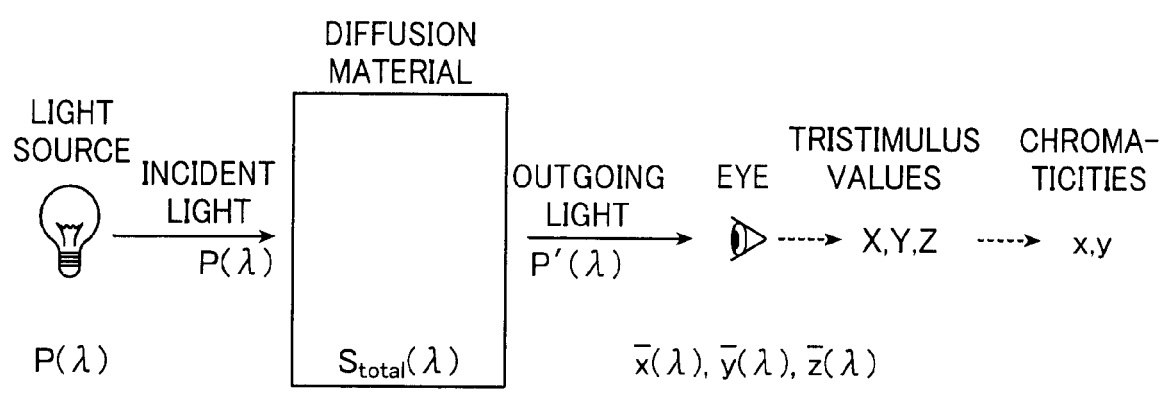
FIG. 1 is an explanatory view schematically showing the wavelength dependency of emitted light generated in a diffusion material of the present invention, and the color tone of the light to be sensed by the human eye.

FIG. 1 is an explanatory view schematically showing the wavelength dependency of emitted light generated in the diffusion material of the present invention, and the color tone of the light to be sensed by the human eye.

That is, when light enters the diffusion material, the human being feels the "color tone" of emitted light according to the process as shown in FIG. 1.

1) In FIG. 1, light outgoing from a light source enters the diffusion material with a spectral distribution $P(\lambda)$. That is, an input to the diffusion material is the spectral distribution $P(\lambda)$.

2) The light entering the diffusion material travels in the material while being scattered in dependence on a total cross-sectional area of scattering $S_{total}(\lambda)$ at each wavelength, and then outgoes with a spectral distribution $P'(\lambda)$. Therefore, an output from the diffusion material is the spectral distribution $P'(\lambda)$.

3) The light that enters the human eye is converted into color information amounts X, Y, and Z (tristimulus values) as shown in the following expression (5) by using the red response sensitivity $\bar{x}(\lambda)$, green response sensitivity $\bar{y}(\lambda)$, and blue response sensitivity $\bar{z}(\lambda)$ of the human being as color matching functions.

4) The tristimulus values X, Y, and Z are converted into chromaticities x and y by the following expression (6). Here, (x, y) are plotted as a chromaticity diagram.

$$\begin{cases} X' = \int_\lambda P'(\lambda)\bar{x}(\lambda)d\lambda \\ Y' = \int_\lambda P'(\lambda)\bar{y}(\lambda)d\lambda \\ Z' = \int_\lambda P'(\lambda)\bar{z}(\lambda)d\lambda \end{cases} \begin{cases} X = \int_\lambda P(\lambda)\bar{x}(\lambda)d\lambda \\ Y = \int_\lambda P(\lambda)\bar{y}(\lambda)d\lambda \\ Z = \int_\lambda P(\lambda)\bar{z}(\lambda)d\lambda \end{cases} \quad \ldots(5)$$

In the expression, X', Y', and Z' represent the tristimulus values of the emitted light, X, Y, and Z represent the tristimulus values of the incident light, and xbar, ybar, and zbar represent color matching functions.

$$\begin{cases} x' = \dfrac{X'}{X'+Y'+Z'} \\ y' = \dfrac{Y'}{X'+Y'+Z'} \end{cases} \begin{cases} x = \dfrac{X}{X+Y+Z} \\ y = \dfrac{Y}{X+Y+Z} \end{cases} \quad (6)$$

The present invention aims to keep the shape of each of the spectral distribution $P(\lambda)$ of the incident light and the spectral distribution $P'(\lambda)$ of the outgoing light nearly unchanged, and is based on an approach to controlling the total cross-sectional area of scattering $S_{total}(\lambda)$ at each wavelength.

1) Therefore, a diffusion material which is of interest in the present invention is as follows: visible light entering the material is diffused in the material, and is then emitted, and the material emits the incident light as the emitted light to its outside without changing the wavelength dependency of the incident light.

2) Accordingly, the present invention adjusts a diffusion function in the diffusion material so that chromaticity variations $\Delta x$ and $\Delta y$ of emitted light with respect to incident light (from a light source) each fall within a predetermined range where a human being does not recognize the variation as color unevenness, or preferably is 0.03 or less each as shown in the following expression (9). It should be noted that the chromaticity variations $\Delta x$ and $\Delta y$ are determined by the following expression (7).

$-0.03 \leq \Delta x \leq 0.03$ $-0.03 \leq \Delta y \leq 0.03$ \quad (9)

In the present invention, incident light can be turned into emitted light free from wavelength unevenness and color difference by causing each of the chromaticity variations $\Delta x$ and $\Delta y$, which are recognized as color changes or color unevenness by the visual sense of a human being, to fall within a predetermined range, or preferably satisfy the above expression (9).

$\Delta x = x' - x$ $\Delta x = y' - y$ \quad (7)

In the expression, x and y represent the chromaticities of the incident light (light source), and x' and y' represent the chromaticities of the emitted light.

3) A constant of proportionality $C(\lambda)$ represented by the following expression (4) is adjusted so that the above expression (9) is satisfied. Here, the constant of proportionality $C(\lambda)$ is a light intensity attenuating rate in the diffusion material;

provided that the tristimulus values X, Y, and Z needed in determining the chromaticities of incident light and outgoing light are represented by the above expressions (5) and (6).

$$P'(\lambda) = C(\lambda) P(\lambda) \quad (4)$$

4) The total cross-sectional area of scattering $S_{total}(\lambda)$ in the diffusion material is adjusted in accordance with the following expression (3) so that a condition for the light intensity attenuating rate $C(\lambda)$ determined in the above expression (4) is satisfied.

$$C(\lambda) = \exp[-S_{total}(\lambda) \cdot L] \quad (3)$$

In the expression, L represents the thickness of the diffusion material. The light intensity attenuating rate $C(\lambda)$ is determined by the total cross-sectional area of scattering $S_{total}(\lambda)$ of the fine particles mixed in the diffusion material and a distance L along which light that vertically enters the diffusion material propagates in the diffusion material.

As described above, the present invention aims to emit incident light as emitted light to the outside without changing the wavelength dependency of the incident light, so the shape of each of the spectral distribution $P(\lambda)$ of the incident light and the spectral distribution $P'(\lambda)$ of the outgoing light is kept nearly unchanged, and the total cross-sectional area of scattering $S_{total}(\lambda)$ at each wavelength is controlled. Accordingly, the following expression (11) is ideally valid. Here, B, G, and R represent three major wavelengths included in incident visible light, and correspond to a blue color, a green color, and a red color, respectively. It should be noted that the representative wavelength of the red color (R) of light outgoing from a light source may be set to 435 [nm], the representative wavelength of the green color (G) of the light may be set to 545 [nm], and the representative wavelength of the blue color (B) of the light may be set to 615 [nm].

$$C(B)/C(G) \approx C(R)/C(G)$$

$$S_{total}(B)/S_{total}(G) \approx S_{total}(R)/S_{total}(G)$$

$$S_{total}(B)/S_{total}(R) \approx 1 \quad (11)$$

However, the present invention adjusts the diffusion function in the diffusion material so that the chromaticity variations $\Delta x$ and $\Delta y$ of emitted light with respect to incident light is each 0.03 or less as shown in the above expression (9). Accordingly, a ratio of the total cross-sectional areas of scattering $S_{total}(B)/S_{total}(R)$ in the diffusion material between blue light (B) and red light (R) generally has an allowable range given by the following expression (10):

$$K\min \leq S_{total}(B)/S_{total}(R) \leq K\max \quad (10)$$

where Kmin and Kmax represent the minimum value and maximum value, respectively, of the ratio of the total cross-sectional areas of scattering in the diffusion material at which illumination light formed of white light free from wavelength unevenness and color unevenness can be emitted.

By the way, the total cross-sectional area of scattering $S_{total}(\lambda)$ in the diffusion material as a total of the cross-sectional areas of scattering of fine particles as all scatterers dispersed in the diffusion material in light having a wavelength of $\lambda$ can be determined as described below.

a. First, the case where a diffusion particle has multiple particle diameters (n kinds) will be described.

In this case, the total cross-sectional area of scattering $S_{total}(\lambda)$ in the diffusion material can be determined by the following expressions (1), (2-1), and (2).

That is, in the present invention, a relative refractive index between each of the selected multiple fine particles and a matrix, for example, a relative refractive index $m_i$ between an i-th fine particle and the matrix is determined from the following expression (1). Then, the total cross-sectional area of scattering $Sr(\lambda)$ of the entirety of fine particles each having a particle diameter of $r_i$ (i-th) is determined from the following expression (2-1) by using the relative refractive index $m_i$ thus determined, and the total cross-sectional area of scattering $S_{total}(\lambda)$ in the diffusion material is determined from the following expression (2).

$$m_i = n_{pi}(\lambda)/n_m(\lambda) \quad (1)$$

$$S_r(\lambda) = N \sum_{i=1}^{\infty} S_i(m_i, \lambda) F(r_i) \quad (2\text{-}1)$$

$$S_{total}(\lambda) = \sum_{i=1}^{n} S_i(\lambda) N A_i, \quad \sum_{i=1}^{n} A_i = 1 \quad (2)$$

In the expressions, $n_m(\lambda)$ represents the refractive index $n_m$ of the matrix, $n_{pi}(\lambda)$ represents the refractive index of each of fine particles of an i-th kind (i=2, ..., n) (also referred to as "i-th fine particles"), $A_i$ represents the blending ratio at which the i-th fine particles are blended, $r_i$ represents the particle size of each of the i-th fine particles, $F(r_i)$ represents the particle size distribution function of each of multiple kinds of fine particles, $m_i$ represents the relative refractive index between each of the i-th fine particles and the matrix, $S_i(m_i, \lambda)$ represents the cross-sectional area of scattering of each of the i-th fine particles determined by Mie theory, and N represents the number density of the fine particles in the diffusion material represented in a unit of, for example, [particles/m$^3$].

It should be noted that the particle size distribution function $F(r)$ of a fine particle corresponds to a particle size distribution possessed by the particle diameters of a fine particle used as a scatterer, and is generally represented as shown in the following expression (8). The expression (8) represents the case where the distribution is discrete, for example, the case where the distribution forms a binomial distribution.

$$F(r) = \frac{1}{\sqrt{2\pi Npq}} \exp - \frac{(r - Np)^2}{2Npq}, \quad q = 1 - p \quad (8)$$

where $N_0$ represents the total number of particles, $F(r)$ represents the number of particles each having a particle diameter of r, p represents the probability that a particle having a particle diameter of r is present, Np represents an average particle diameter, and Npq represents a variance.

By the way, in the above-mentioned example, the cross-sectional area of scattering of each of the i-th fine particles determined by Mie theory out of the selected multiple fine particles is represented by $S_i(m_i, \lambda)$, the particle size distribution of each of the selected multiple fine particles is represented by $F(r)$, the total cross-sectional area of scattering $Sr(\lambda)$ of the entirety of fine particles each having a particle diameter of $r_i$ (i-th) is determined from the above expression (2-1), and the total cross-sectional area of scattering $S_{total}(\lambda)$ in the diffusion material is determined from the above expression (2). Further, the above expression (8) is given as a specific example of the particle size distribution $F(r)$ in that case. However, the present invention is not limited to the foregoing, and the total cross-sectional area of scattering $S_{total}(\lambda)$ in the diffusion material may be determined from the following expression (2-2) instead of the above expression (2-1) and from the above expression (2) by representing the cross-sectional area of scattering of each of the i-th fine particles by $S_i(\delta, m_i, \lambda)$ and the particle size distribution function of each of the i-th fine particles by $f_i(\delta)$ where $\delta$ represents the particle size of a fine particle.

With regard to the particle size distribution function $f_i(\delta)$ of each of the i-th fine particles in this case, a particle size distribution function $f_i(\delta)$ represented by the following expression (8-1) may be used instead of the above expression (8) when the particle size distribution of each of the selected multiple fine particles can be regarded as forming, for example, a normal distribution.

$$S_i(\lambda) = N \int_0^\infty S_i(\delta, mi, \lambda) f_i(\delta) d\delta \qquad (2\text{-}2)$$

$$S_{total}(\lambda) = \sum_{i=1}^n S_i(\lambda) N A_i \quad \sum_{i=1}^n A_i = 1 \qquad (2)$$

$$f_i(\delta) = \frac{1}{\sigma_i \sqrt{2\pi}} \exp\left[-\frac{1}{2}\left(\frac{\delta - \mu_i}{\sigma_i}\right)^2\right] \qquad (8\text{-}1)$$

where $\mu_i$ represents the average particle diameter of the i-th fine particles, and $\sigma_i$ represents the standard deviation of the average particle diameter.

b. Next, the case where the diffusion particles each have a single particle diameter (one kind) will be described.

In this case, the total cross-sectional area of scattering $S_{total}(\lambda)$ in the diffusion material can be determined from the following expressions (1-1) and (2-3) by using the cross-sectional area of scattering $S(\delta, m, \lambda)$ of each of the fine particles determined by Mie theory when the refractive index of each of the fine particles is represented by $n_p(\lambda)$, the particle size distribution function of each of the fine particles at a particle diameter $\delta$ of each of the fine particles is represented by $f(\delta)$, and a relative refractive index between each of the fine particles and the matrix is represented by m.

It should be noted that, when the particle size distribution of each of the fine particles forms a normal distribution in this case, it is sufficient to use a distribution function represented by the following expression (8-2) as a particle size distribution function $f(\delta)$; when the particle size distribution of each of the fine particles is discrete, for example, the distribution forms a binomial distribution, it is sufficient to use the distribution function $F(r)$ represented by the above expression (8) instead of the following particle size distribution function $f(\delta)$.

$$m = n_p(\lambda)/n_m(\lambda) \qquad (1\text{-}1)$$

$$S_{total}(\lambda) = N \int_0^\infty S(\delta, m, \lambda) f(\delta) d\delta \qquad (2\text{-}3)$$

$$f(\delta) = \frac{1}{\sigma\sqrt{2\pi}} \exp\left[-\frac{1}{2}\left(\frac{\delta - \mu}{\sigma}\right)^2\right] \qquad (8\text{-}2)$$

where $\mu$ represents an average particle diameter, and $\sigma$ represents a standard deviation.

It should be noted that, as described above, the term "multiple kinds of fine particles each having a refractive index different from that of the matrix of a diffusion material to be dispersed in the diffusion material" as used in the present invention includes fine particles of all kinds except a fine particle having a single particle diameter. For example, fine particles made of the same material, having the same refractive index, and different from each other only in particle size or particle size distribution are permitted, and fine particles each merely having a particle size distribution are also permitted. Of course, fine particles different from each other in one or both of material and refractive index are also permitted. Further, when the fine particles to be dispersed in the matrix are different from each other in one or both of material and refractive index, the fine particles may be fine particles each having a single particle diameter, or may be fine particles each having a particle size distribution. It should be noted that, when multiple kinds of fine particles are regarded as multiple kinds of fine particles because of their predetermined particle size distributions as described above, it is sufficient to regard the respective particle sizes to be distributed as one kind in each of the above aspects; in the present invention, the total cross-sectional area of scattering $S_{total}(\lambda)$ in the diffusion material may be determined by regarding the fine particles as fine particles of one kind each having the above-mentioned predetermined particle size distribution and calculating each of the above expressions with i=n=1 (one kind) in each of the above aspects.

Next, the method of evaluating a diffusion material according to the first aspect of the present invention using the above-mentioned novel technique of the present invention will be described.

The method of evaluating a diffusion material of the present invention involves: determining a total cross-sectional area of scattering $S_{total}(\lambda)$ in the diffusion material from the above expression (2) as a total of the cross-sectional areas of scattering $S(\lambda)$ of respective fine particles that are determined by Mie theory for all of multiple kinds of fine particles dispersed in a matrix at a wavelength $\lambda$ of incident light entering the diffusion material; determining a light intensity attenuating rate $C(\lambda)$ in the diffusion material by using the total cross-sectional area of scattering $S_{total}(\lambda)$ from the above expression (3); determining chromaticity variations $\Delta x$ and $\Delta y$ of emitted light outgoing from the diffusion material with respect to the incident light entering the diffusion material by using the attenuating rate $C(\lambda)$; and evaluating the diffusion material for diffusion power by using the chromaticity variations $\Delta x$ and $\Delta y$ of the outgoing light with respect to the incident light thus obtained. The method is preferably as follows: when the chromaticity variations $\Delta x$ and $\Delta y$ of the outgoing light with respect to the incident light each satisfy the above expression (9), illumination light such as white light free from wavelength unevenness and color unevenness can be emitted, and the diffusion material is judged to have high diffusion power, but, when the chromaticity variations $\Delta x$ and $\Delta y$ do not satisfy the above expression (9), the diffusion material is judged to have low diffusion power.

Here, the total cross-sectional area of scattering $S_{total}(\lambda)$ in the diffusion material is preferably determined from the above expressions (2-1) and (2) by using a relative refractive index $m_i$ between each of the i-th fine particles and the matrix determined from the above expression (1), the mi being obtained from the above expression (1) using a refractive index $n_m(\lambda)$ of the matrix, a refractive index $n_{pi}(\lambda)$ of each of i-th fine particles, a blending ratio $A_i$ at which the i-th fine particles are mixed, a particle size $r_i$ of each of the i-th fine particles, a particle size distribution function $F(r_i)$ of each of multiple kinds of fine particles, a relative refractive index $m_i$ between each of the i-th fine particles and the matrix determined from the above expression (1), a cross-sectional area of scattering $S_i(m_i, \lambda)$ of each of the i-th fine particles, a thickness L of the diffusion material, and a number density N of the fine particles in the diffusion material. It should be noted that, in this case, a particle size distribution function represented by the above expression (8) is desirably used as the particle size distribution function F(r) of each of the fine particles.

In this case, the total cross-sectional area of scattering $S_{total}(\lambda)$ in the diffusion material may be determined from the above expressions (2-2) and (2) by using a particle size $\delta$ of a fine particle, a particle size distribution function $f_i(\delta)$ of each of the i-th fine particles, and a cross-sectional area of scattering $S_i(\delta, m_i, \lambda)$ of each of the i-th fine particles instead of the particle size $r_i$ of each of the i-th fine particles, the particle size distribution function $F(r_i)$ of each of the multiple kinds of fine particles, and the cross-sectional area of scattering $S_i(m_i, \lambda)$ of each of the i-th fine particles described above. It should be noted that, in this case, the particle size distribution of each of the fine particles may be regarded as forming a normal distribution, and a particle size distribution function represented by the above expression (8-1) may be used as the particle size distribution function $f_i(\delta)$ instead of the particle size distribution function F(r) of each of the fine particles.

Next, the light intensity attenuating rate $C(\lambda)$ in the diffusion material is determined from the above expression (3) by using the total cross-sectional area of scattering $S_{total}(\lambda)$ in the diffusion material thus obtained.

Subsequently, an intensity $P'(\lambda)$ of the emitted light outgoing from the diffusion material is determined from the above expression (4) by using the light intensity attenuating rate $C(\lambda)$ thus determined and an intensity $P(\lambda)$ of the incident light entering the diffusion material.

Chromaticities x and y of the incident light, and chromaticities x' and y' of the emitted light are determined from the above expressions (5) and (6) by using the intensity $P'(\lambda)$ of the emitted light thus obtained and the intensity $P(\lambda)$ of the incident light.

The chromaticity variations $\Delta x$ and $\Delta y$ of the outgoing light with respect to the incident light are determined from the above expression (7) by using the chromaticities x and y of the incident light, and the chromaticities x' and y' of the emitted light thus obtained.

Finally, as described above, the diffusion material can be evaluated for diffusion power depending on whether or not the chromaticity variations $\Delta x$ and $\Delta y$ of the outgoing light with respect to the incident light thus obtained each fall within a predetermined range, or each preferably satisfy the above expression (9).

Thus, in the evaluating method of the present invention, the diffusion material can be accurately evaluated for scattering power. Further, in the evaluating method of the present invention, even when a fine particle having a particle size distribution is added, or even when a fine particle having large wavelength dependency is used, whether a chromaticity variation of emitted light outgoing from the diffusion material with respect to incident light entering the diffusion material falls within a certain range can be accurately judged, so whether the diffusion material can emit illumination light formed of white light free from wavelength unevenness can be accurately judged, that is, the diffusion material can be accurately evaluated for scattering power.

In addition, the diffusion material according to the second aspect of the present invention is judged to satisfy the above expression (9) by the evaluating method of the present invention. Therefore, the diffusion material according to the second aspect of the present invention judged to have high diffusion power by the evaluating method of the present invention can emit illumination light formed of white light free from wavelength unevenness.

A material to be used as the matrix of the diffusion material of the present invention is not particularly limited. Any material may be used as long as the material is used as the matrix of the diffusion material, and any one of all conventionally known materials for a matrix is applicable. For example, any one of the methacrylic resins disclosed in JP 11-19928 A and JP 11-21357 A typified by polymethyl methacrylate (PMMA) can be used.

In addition, fine particles to be used as scatterers in the diffusion material of the present invention are not particularly limited. Any fine particles may be used as long as the fine particles are used as the scatterers of the diffusion material, and any one of all conventionally known materials for scattered fine particles is applicable. For example, silicone resin fine particles as typified by solid, cross-linkable silicone resin fine particles disclosed in JP 11-19928 A and JP 11-21357 A can be used. In addition, in the present invention, the shape of each fine particle, which is desirably a true spherical shape, is not limited to the true spherical shape, and any shape is permitted.

Next, the method of blending fine particles in a diffusion material according to the third aspect of the present invention will be described.

The method of blending fine particles in a diffusion material of the present invention involves appropriately determining the blending amounts of multiple kinds of fine particles each having a refractive index different from that of a matrix upon dispersion of the multiple kinds of fine particles as scatterers in the matrix in order that desired diffusion power may be obtained in a diffusion material in which the multiple kinds of fine particles are dispersed in the matrix.

In contrast to the evaluating method of the present invention, in the blending method of the present invention, first, the light intensity attenuating rate $C(\lambda)$ in the diffusion material is determined so that the chromaticity variations $\Delta x$ and $\Delta y$ of emitted light outgoing from the diffusion material with respect to incident light entering the diffusion material each satisfy the above expression (9).

The total cross-sectional area of scattering $S_{total}(\lambda)$ in the diffusion material is determined from the above expression (3) at a wavelength $\lambda$ of the incident light entering the diffusion material so that a condition for the light intensity attenuating rate $C(\lambda)$ in the diffusion material thus obtained is satisfied.

Next, the blending amounts $A_i$ of the multiple kinds of fine particles dispersed in the matrix are determined from the above expression (2) so that the total cross-sectional area of scattering $S_{total}(\lambda)$ in the diffusion material thus determined is determined as a total of the cross-sectional areas of scattering $S(\lambda)$ of respective fine particles that are determined by Mie theory for all of the multiple kinds of fine particles.

In the blending method of the present invention, the multiple kinds of fine particles are blended in the matrix in accordance with the blending amounts thus determined.

Here, the blending method of the present invention preferably involves: determining the chromaticities x and y of the incident light, and the chromaticities x' and y' of the emitted light by using the above expression (7) from the chromaticity variations $\Delta x$ and $\Delta y$ of the outgoing light with respect to the incident light each satisfying the above expression (9); determining the intensity $P'(\lambda)$ of the outgoing light and the intensity $P(\lambda)$ of the incident light by using the above expressions (5) and (6); determining the light intensity attenuating rate $C(\lambda)$ in the diffusion material by using the above expression (4); and determining the total cross-sectional area of scattering $S_{total}(\lambda)$ in the diffusion material by using the above expression (3).

Then, suppose that the three major wavelengths of the incident light entering the diffusion material are represented by B (blue light), G (green light), and R (red light), it is desirable to determine the range of the ratio $S_{total}(B)/S_{total}(R)$ of the total cross-sectional area of scattering in blue light to the total cross-sectional area of scattering in red light, that is, the upper limit Kmax and the lower limit Kmin represented by the above expression (10).

After that, as described in detail below, the blending ratio $A_i$ at which the i-th fine particles are blended can be determined from the above expressions (2-1) or (2-2), and (2) by using the range of the total cross-sectional areas of scattering $S_{total}(B)$ and $S_{total}(R)$ in the diffusion material thus determined.

The blending amounts of the multiple kinds of fine particles thus obtained are determined so that the chromaticity variations of the outgoing light with respect to the incident light in the diffusion material in which those multiple kinds of fine particles are dispersed in the matrix each satisfy the above expression (9), and the ratio of the total cross-sectional area of scattering in blue light to the total cross-sectional area of scattering in red light satisfies the above expression (10). Accordingly, even when a fine particle having a particle size distribution is added, or even when a fine particle having large wavelength dependency is used, a diffusion material capable of emitting illumination light formed of white light free from wavelength unevenness can be obtained.

Although the above-mentioned example of the blending method of the present invention involves determining the allowable range of the light intensity attenuating rate $C(\lambda)$ in the order opposite to that of the evaluating method of the present invention, and determining the range of the ratio $S_{total}(B)/S_{total}(R)$ of the total cross-sectional area of scattering in blue light to the total cross-sectional area of scattering in red light, or the upper limit Kmax and the lower limit Kmin, the present invention is not limited to the foregoing, and the blending method of the present invention may involve determining the allowable range of the light intensity attenuating rate $C(\lambda)$ and the allowable range of a particle diameter in the same order as that of the evaluating method of the present invention, and determining the range of the ratio $S_{total}(B)/S_{total}(R)$ of the total cross-sectional area of scattering in blue light to the total cross-sectional area of scattering in red light, or the upper limit Kmax and the lower limit Kmin by using the allowable ranges.

In addition, the method of producing a diffusion material according to the fourth aspect of the present invention involves melting, mixing, and dispersing multiple kinds of fine particles blended in accordance with blending amounts determined by the blending method of the present invention in a matrix. Therefore, a diffusion material produced by the production method of the present invention has high diffusion power, and can emit illumination light formed of white light free from wavelength unevenness.

The method of producing a diffusion material of the present invention is not particularly limited except for the determination of the loading. Any method may be employed, and any one of all conventionally known production methods is applicable. For example, any one of the production methods disclosed in JP 11-19928 A and JP 11-21357 A is applicable.

Next, an example of an algorithm for carrying out the method of evaluating a diffusion material and method of blending fine particles in a diffusion material of the present invention each using the above-mentioned novel technique of the present invention will be described.

Figure 2:
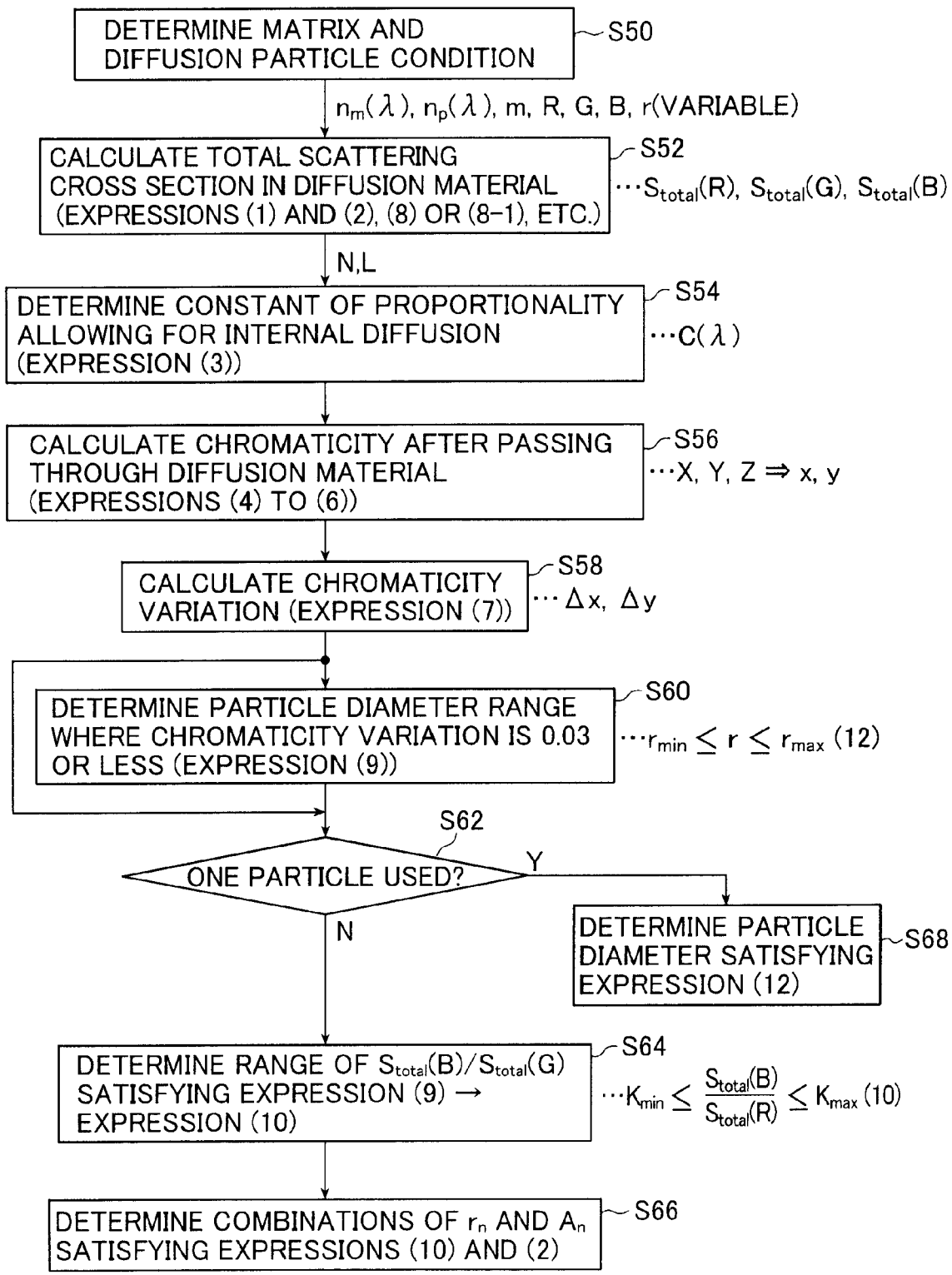
FIG. 2 is an example of a flow chart showing an example of an algorithm for a method of evaluating a diffusion material of the present invention and a method of blending fine particles in a diffusion material of the present invention.

FIG. 2 is an example of a flow chart showing the example of the algorithm for the method of evaluating a diffusion material and method of blending fine particles in a diffusion material of the present invention.

First, in Step S50, fine particles having different refractive indices are dispersed in a material serving as a matrix, and a particle condition under which emitted light is not observed to have any wavelength unevenness is determined.

Here, the refractive index of the matrix is represented by $n_m(\lambda)$, the refractive index of each of i-th fine particles is represented by $n_{pi}(\lambda)$, the particle size of a fine particle is represented by r, the particle size distribution function of each of multiple kinds of fine particles is represented by $F(r_i)$ or $f_i(r)$, the thickness (optical path length) of a diffusion material is represented by L[m], the number density of the fine particles in the diffusion material is represented by N [particles/m³], and the three major wavelengths of a visible light source to be used are represented by B, G, and R [nm].

In this case, the particle diameter r of a fine particle is a variable, so an initial value should be substituted.

Next, in Step S52, in accordance with the above expressions (1), (2-1) or (2-2), (2), and (8) or (8-1), a relative refractive index $m_i$ between each of the i-th fine particles and the matrix is determined, and, furthermore, a total cross-sectional area of scattering $S_{total}(\lambda)$ in the diffusion material is determined by using a cross-sectional area of scattering $S_i(m_i, \lambda)$ or $S_i(\delta, m_i, \lambda)$ of each of the i-th fine particles.

It should be noted that, when fine particles of one kind are used in Step S52, the total cross-sectional area of scattering $S_{total}(\lambda)$ in the diffusion material is determined by using the above expressions (1-1), (2-3), and (8-2) for each corresponding particle condition.

Subsequently, in Step S54, a light intensity attenuating rate $C(\lambda)$ in the diffusion material is determined by using the above expression (3) from the total cross-sectional area of scattering $S_{total}(\lambda)$ in the diffusion material.

Next, in Step S56, chromaticities x and y of incident light entering the diffusion material, and chromaticities x' and y' of emitted light outgoing from the diffusion material are determined by using the above expressions (4) to (6) from the light intensity attenuating rate $C(\lambda)$ in the diffusion material via an intensity $P(\lambda)$ of the incident light and an intensity $P'(\lambda)$ of the emitted light, and tristimulus values X, Y, and Z of the incident light and tristimulus values X', Y', and Z' of the emitted light.

Next, in Step S58, chromaticity variations $\Delta x$ and $\Delta y$ of the outgoing light with respect to the incident light are determined from the above expression (7) by using the chromaticities x and y of the incident light, and the chromaticities x' and y' of the emitted light thus obtained.

In the evaluating method of the present invention, finally, in Step S60, the diffusion material can be evaluated for diffusion power depending on whether the chromaticity variations $\Delta x$ and $\Delta y$ of the outgoing light with respect to the incident light thus obtained each satisfy the above expression (9), that is, the variations each have an absolute value of 0.03 or less.

In the method of blending fine particles in a diffusion material of the present invention, in Step S60, a particle diameter range where the variations each satisfy the above expression (9), that is, the variations each have an absolute value of 0.03 or less is determined. Thus obtained is the following expression (12) satisfying the above expression (9), where rmax and rmin are the upper and the lower limits of the particle diameter range.

$$rmin \leq r \leq rmax \qquad (12)$$

Next, in Step S62, judgment as to whether the number of fine particles to be used as scatterers is one (one kind) is made. When the number is not one (NO), the procedure moves to Step S64. When the number is one (one kind: YES), the procedure moves to Step S68, and a particle diameter satisfying the above expression (12) is determined.

In the blending method of the present invention, when the fact that multiple kinds of fine particles will be used is known in advance, the procedure may jump from Step S58 straight to Step S62 skipping Step S60, or may jump from Step S58 straight to Step S64 skipping both Steps S60 and S62.

In Step S64, the range of a ratio $S_{total}(B)/S_{total}(R)$ of the total cross-sectional area of scattering in blue light satisfying the above expression (9) to the total cross-sectional area of scattering in red light satisfying the above expression (9) is determined. That is, the upper limit Kmax and the lower limit Kmin in the above expression (10) are determined.

In the blending method of the present invention, finally, in Step S66, a combination of a particle size $r_i$ of each of the i-th fine particles and a blending ratio $A_i$ at which the i-th fine particles are mixed (i=1 to n) satisfying the range of the above expression (10) and the above expression (2) is determined.

Thus, in the blending method of the present invention, the blending amounts of the multiple kinds of fine particles to be dispersed in the matrix can be determined.

Thus, in the present invention, even when a fine particle having a particle size distribution is added, or even when a fine particle having large wavelength dependency is used, a diffusion material capable of emitting illumination light formed of white light free from wavelength unevenness can be obtained.

EXAMPLES

Hereinafter, the present invention will be specifically described on the basis of examples.

Example 1

In Example 1, the method of evaluating a diffusion material and method of blending fine particles in a diffusion material of the present invention were actually performed as described below by using a matrix and diffusion particles in accordance with the flow chart shown in FIG. 2.

1) Constitution of Diffusion Material

Base material: PMMA (refractive index $n_D$=1.492)

Fine particles: Tospearl (silicone resin fine particles manufactured by GE Silicones, $n_D$=1.44)

Light source: CCFL (R=435 [nm], G=545 [nm], B=615 [nm])

Figure 3:
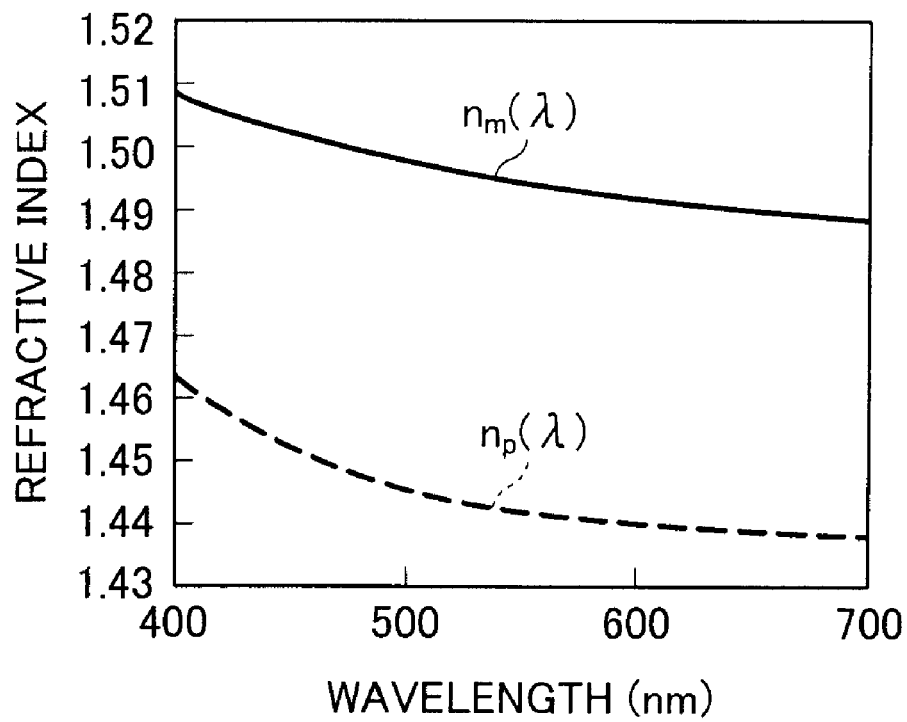
FIG. 3 is a graph showing the wavelength dependency ($n(\lambda)$) of the refractive index of each of a matrix and a fine particle in an example of the present invention.
Figure 4:
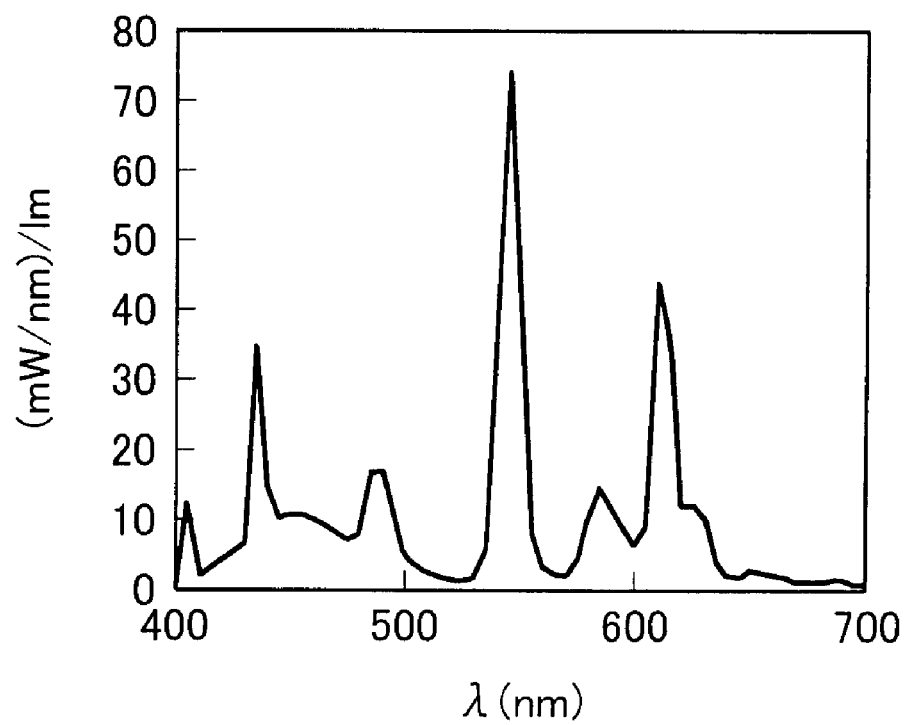
FIG. 4 is a graph showing the spectral characteristics of a light source used in an example of the present invention.

FIG. 3 shows the wavelength dependency ($n(\lambda)$) of the refractive index of each of PMMA and the Tospearl, and FIG. 4 shows the spectral characteristics of the CCFL.

Thus, conditions for the matrix and the diffusion particles in Step S50 of FIG. 2 were determined.

2) Calculation of Chromaticity Variations ($\Delta x$, $\Delta y$)

Fine particle concentration: 0.5 vol % (converted into the particle density N [particles/m³] at each particle diameter)

Optical path length: L=1.0 [mm]

Figure 5:
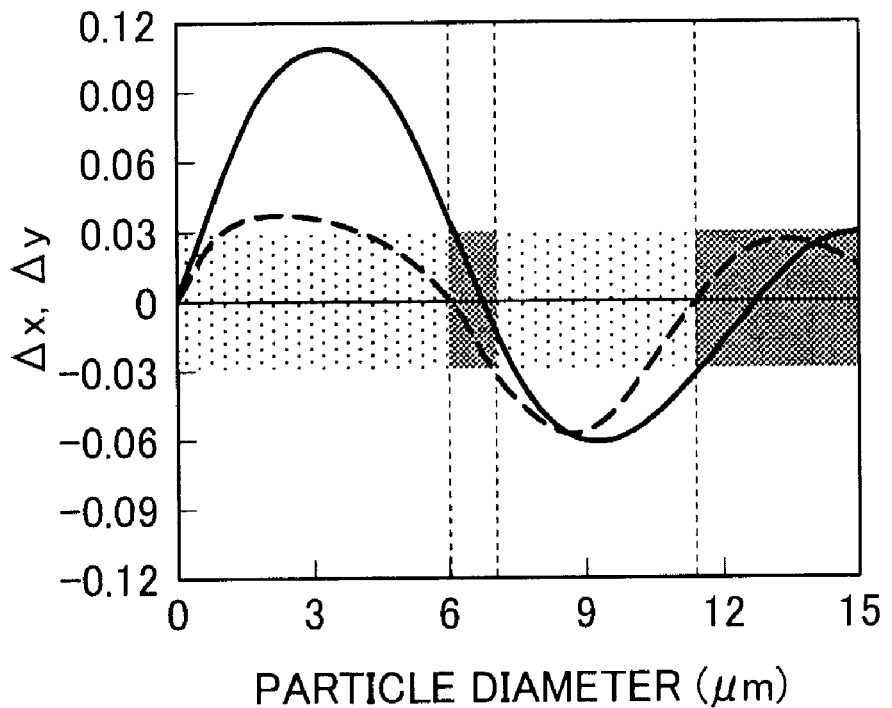
FIG. 5 is a graph showing a relationship between a particle diameter r of a dispersed fine particle and chromaticity variations ($\Delta x$, $\Delta y$) in an example of the present invention.

Steps S52 to S58 of FIG. 2 were performed under those conditions, whereby chromaticity variations ($\Delta x$, $\Delta y$) were calculated. FIG. 5 shows the results. FIG. 5 is a graph showing a relationship between the "particle diameter (μm)" of a dispersed fine particle and the chromaticity variations ($\Delta x$, $\Delta y$).

3) Determination of Particle Diameter Range where Human Being does not Visually Feel any Wavelength Unevenness In Step S60, a particle diameter range where the chromaticity variations each satisfied the above expression (9), that is, the variations each had an absolute value of 0.03 or less was determined from FIG. 5.

As can be seen from FIG. 5, the particle diameter range where the chromaticity variations each satisfy the above expression (9), that is, the variations each have an absolute value of 0.03 or less is as described below (the above expression (12)).

$6.1 \leq r \leq 7.5, 11.4 \leq r \leq 14.7$ [μm]

4) Determination of Range of $S_{Total}(B)/S_{Total}(R)$ Corresponding to Expression (10)

Figure 6:
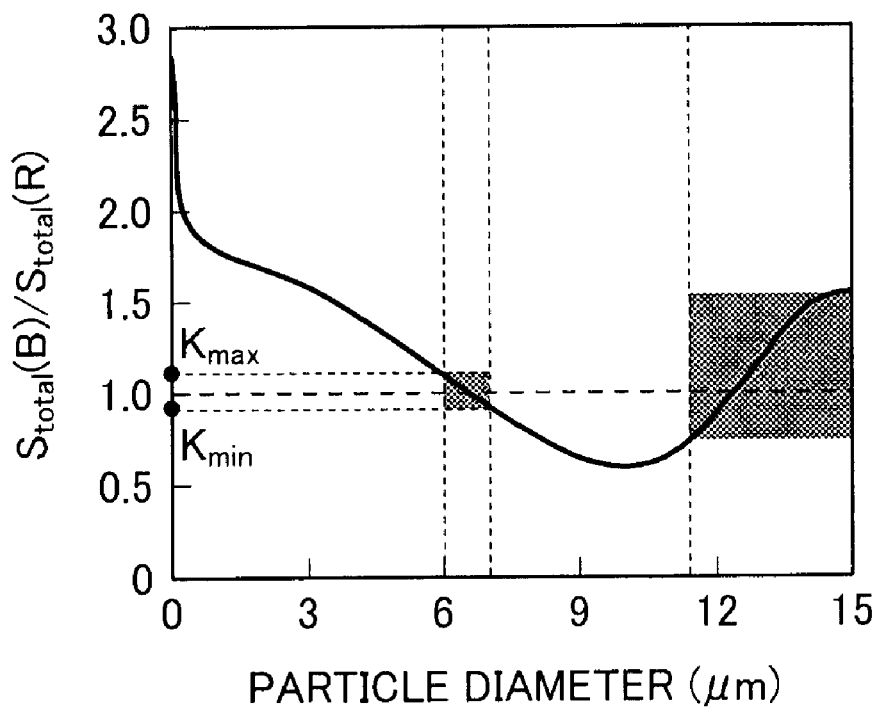
FIG. 6 is a graph showing a relationship between the particle diameter r of the dispersed fine particle and a ratio $S_{total}(B)/S_{total}(R)$ between total cross-sectional areas of scattering in an example of the present invention.

In Step S64, the range of the ratio of the total cross-sectional area of scattering $S_{total}(B)/S_{total}(R)$ satisfying the above expression (9) was determined. FIG. 6 shows the results. FIG. 6 is a graph showing a relationship between the "particle diameter (μm)" of a dispersed fine particle and the ratio of the total cross-sectional area of scattering $S_{total}(B)/S_{total}(R)$. As can be seen from FIGS. 5 and 6, a range corresponding to the particle diameter range where the chromaticity variations each satisfy the above expression (9), that is, the variations each have an absolute value of 0.03 or less is such that Kmin and Kmax given by the following expression (10) are 0.9 and 1.1, respectively.

$$0.9 = K\min \leq S_{total}(B)/S_{total}(R) \leq K\max = 1.1 \quad (10)$$

5) Determination of Particle Diameter of Fine Particle to Be Used a. When One Particle Diameter (One Kind) is Used In Step S68, it is sufficient to determine the particle diameter of a fine particle to be used from the following particle diameter range represented by the above expression (12) determined in the above section (3) from FIG. 5.

$6.1 \leq r \leq 7.5, 11.4 \leq r \leq 14.7$ [μm]

b. When Multiple Kinds of Fine Particles are Blended

In Step S66, it is sufficient to determine the particle diameters and blending amounts (blending ratios) of fine particles to be used from the range between the Kmin and the Kmax represented by the above expression (10) determined from FIG. 6 satisfying the above expressions (10) and (2) in the above section (4).

6) Determination of Blending Amounts (Blending Ratios) of Particles

Next, the determination of the particle diameters and blending amounts (blending ratios) of fine particles to be used to be performed in Step S66 will be described.

Here, for example, the blending ratios of the following two particles (two kinds of fine particles) were determined as described below.

The particle diameters and variances of the two particles (two kinds of fine particles) to be used were as described below.

$r_1$=4.0 [μm], $r_2$=10.0 [μm]

$\sigma_1$=0.5, $\sigma_2$=1.0 (Here, the particle size distributions of both particles were assumed to be normal distributions.)

In this case, the $S_{total}(R)$ and the $S_{total}(B)$ were calculated as described below from the above expressions (1), (2), and (8) or (8-1).

$S_{total\_1}(R)$=0.291×10² [μm²]

$S_{total\_1}(B)$=0.388×10² [μm²]

$S_{total\_2}(R)=1.94\times10^2$ [μm²]

$S_{total\_2}(B)=1.30\times10^2$ [μm²]

The following blending ratios satisfying the above expressions (2) and (12) were determined by using those values.

$0.712 \leq A_1 \leq 0.920$ $0.288 \leq A_2 \leq 0.080$

Thus, the blending ratios of the two particles (two kinds of fine particles) were determined.

It should be noted that, in the present invention, the blending ratios of those multiple kinds of fine particles can be determined even under the following conditions.

At least one particle diameter, in other words, two or more particle diameters (multiple particle diameters having a known particle size distribution)

Mixing of particles made of different materials (multiple kinds of fine particles having known refractive indices and particle size distributions)

Examples 2 to 6 and Comparative Examples 1 to 3 described below were performed in order that the determination of the particle diameter of each of fine particles of one kind and the determination of the blending ratios of multiple kinds of fine particles under the conditions might be described, and an effect of the present invention might be clarified.

Examples 2 to 6 and Comparative Examples 1 to 3

In each of those examples, a matrix and fine particles similar to those of Example 1 were prepared, and the evaluation of a diffusion material and the determination of blending ratios were each performed in the same manner as in Example 1. Conditions for the matrix and diffusion particles used are as described below.

Base material: PMMA (refractive index $n_D=1.492$)

Fine particles: Tospearl (silicone resin fine particles manufactured by GE Silicones, refractive indices $n_D=1.45$ and 1.68, particle diameters r=2.0, 4.0, 6.5, 7.0, 9.0, 10.0, and 11.0)

Light source: CCFL (R=435 [nm], G=545 [nm], B=615 [nm])

Fine Particle Concentration:

0.5 vol % (converted into the particle density N [particles/m³] at each particle diameter)

Optical Path Length (Thickness):

L=1.0 [mm]

Table 1 shows the conditions for the matrix and diffusion particles used in each of Examples 2 to 6 and Comparative Examples 1 to 3, and the obtained results.

TABLE 1

| No. | Particle refractive index | Center particle diameter | Particle diameter variance | Blending ratios | Constant of proportionality | Chromaticity variations | Judgement |
|---|---|---|---|---|---|---|---|
| Example 2 | 1.45 | 6.5 μm | 0.5 | — | $C(B) = 3.24 \times 10^{-2}$<br>$C(G) = 2.66 \times 10^{-2}$<br>$C(R) = 2.66 \times 10^{-2}$ | $\Delta x = 0.012$<br>$\Delta y = 0.021$ | good |
| Comparative Example 1 | 1.45 | 4.0 μm | 0.5 | — | $C(B) = 3.36 \times 10^{-3}$<br>$C(G) = 7.10 \times 10^{-3}$<br>$C(R) = 1.47 \times 10^{-2}$ | $\Delta x = 0.110$<br>$\Delta y = 0.027$ | bad |
| Example 3 | 1.45 | 4.0 μm<br>10.0 μm | 0.5<br>0.5 | 89 vol %<br>11 vol % | $C(B) = 2.46 \times 10^{-3}$<br>$C(G) = 2.67 \times 10^{-3}$<br>$C(R) = 2.46 \times 10^{-3}$ | $\Delta x = 0.003$<br>$\Delta y = 0.010$ | very good |
| Example 4 | 1.45 | 4.0 μm<br>10.0 μm | 0.5<br>0.5 | 92 vol %<br>8 vol % | $C(B) = 3.75 \times 10^{-3}$<br>$C(G) = 4.95 \times 10^{-3}$<br>$C(R) = 5.67 \times 10^{-3}$ | $\Delta x = 0.028$<br>$\Delta y = 0.022$ | good |
| Comparative Example 2 | 1.45 | 4.0 μm<br>10.0 μm | 0.5<br>0.5 | 50 vol %<br>50 vol % | $C(B) = 1.24 \times 10^{-5}$<br>$C(G) = 1.13 \times 10^{-6}$<br>$C(R) = 6.91 \times 10^{-8}$ | $\Delta x = 0.192$<br>$\Delta y = 0.307$ | bad |
| Example 5 | 1.45 | 2.0 μm<br>11.0 μm | 0.5<br>0.5 | 99 vol %<br>1 vol % | $C(B) = 8.29 \times 10^{-3}$<br>$C(G) = 1.15 \times 10^{-2}$<br>$C(R) = 8.29 \times 10^{-3}$ | $\Delta x = 0.004$<br>$\Delta y = 0.012$ | good |
| Example 6 | 1.45<br>1.68 | 9.0 μm<br>7.0 μm | 0.5<br>0.5 | 9 vol %<br>91 vol % | $C(B) = 3.33 \times 10^{-1}$<br>$C(G) = 3.14 \times 10^{-1}$<br>$C(R) = 3.33 \times 10^{-1}$ | $\Delta x = 0.002$<br>$\Delta y = 0.007$ | very good |
| Comparative Example 3 | 1.45<br>1.68 | 9.0 μm<br>7.0 μm | 0.5<br>0.5 | 79 vol %<br>21 vol % | $C(B) = 2.35 \times 10^{-1}$<br>$C(G) = 1.60 \times 10^{-1}$<br>$C(R) = = 1.24 \times 10^{-1}$ | $\Delta x = 0.046$<br>$\Delta y = 0.042$ | bad |

As can be seen from Table 1, Example 2 and Comparative Example 1 are each an example of fine particles of one kind each having a particle size distribution, though the particles used in these examples are different from each other in center particle diameter.

In Example 2, the chromaticity variations ($\Delta x$, $\Delta y$) each have an absolute value of 0.03 or less, that is, each satisfy the above expression (9), and the particle diameter r falls within the range represented by the above expression (12) (see FIG. 5), so white illumination light free from wavelength unevenness (color unevenness) can be emitted. In contrast, in Comparative Example 1, the chromaticity variation ($\Delta x$) has an absolute value in excess of 0.03, that is, does not satisfy the above expression (9), and the particle diameter r deviates from the range represented by the above expression (12) (see FIG. 5), so emitted light shows wavelength unevenness (color unevenness).

Next, Examples 3 and 4, and Comparative Example 2 are different from one another only in blending ratios of two kinds of fine particles. Here, as can be seen from FIG. 5, when the two kinds of fine particles for blending each having a particle diameter of 4.0 μm or 10.0 μm, used in Examples 3 and 4 and Comparative Example 2 are used alone, both of these two kinds of fine particles for blending have the particle diameter r deviating from the range represented by the above expression (12), and at least one of the chromaticity variations (Δx, Δy) has an absolute value in excess of 0.03, which does not satisfy the above expression (9). However, when the two kinds of fine particles are blended at proper blending ratios as in the case of each of Examples 3 and 4, the chromaticity variations (Δx, Δy) can each have an absolute value of 0.03 or less, that is, can each satisfy the above expression (9), so a diffusion material capable of emitting white illumination light free from wavelength unevenness (color unevenness) can be obtained. In Example 3, the absolute value of each of the chromaticity variations (Δx, Δy) can be significantly reduced as compared to that of Example 4.

On the other hand, in Comparative Example 2 in which the two kinds of fine particles are not blended at proper blending ratios, it will be seen that the above expression (9) is not satisfied.

In Example 5, a difference in particle diameter between two kinds of fine particles to be blended is larger than that of each of Examples 3 and 4. However, when the two kinds of fine particles are blended at proper blending ratios, the chromaticity variations (Δx, Δy) can each have an absolute value of 0.03 or less, that is, can each satisfy the above expression (9), so a diffusion material capable of emitting white illumination light free from wavelength unevenness (color unevenness) can be obtained.

In addition, in each of Example 6 and Comparative Example 3, two kinds of fine particles to be blended are different from each other in both particle diameter and refractive index. However, when the two kinds of fine particles are blended at proper blending ratios as in the case of Example 6, the chromaticity variations (Δx, Δy) can each have an absolute value much smaller than 0.03, so a diffusion material capable of emitting white illumination light of which wavelength unevenness (color unevenness) is significantly reduced can be obtained. In contrast, in Comparative Example 3 in which the two kinds of fine particles are not blended at proper blending ratios, none of the chromaticity variations (Δx, Δy) can have an absolute value of 0.03 or less.

The foregoing shows that each of the examples of the present invention has excellent effects, which become obvious in comparison with the comparative examples.

The diffusion material, method of evaluating a diffusion material, method of blending fine particles in a diffusion material, and method of producing a diffusion material according to the present invention have been described above in detail by way of various examples. However, the present invention is not limited to the foregoing, and it goes without saying that various improvements or design modifications may be made without departing from the gist of the present invention.

INDUSTRIAL APPLICABILITY

The diffusion material of the present invention can emit illumination light formed of white light free from wavelength unevenness. Accordingly, the diffusion material can be utilized as: a diffusion material for, for example, a diffusion sheet or diffusion panel for use in, for example, the lighting unit (backlight unit) of a liquid crystal display device; or a diffusion material for use, for example, in a member (screen) for forming an image with an image signal from a projector or in various lighting units.

In addition, a diffusion material can be accurately evaluated for scattering power by the method of evaluating a diffusion material of the present invention. Accordingly, the method can be utilized as a method of evaluating: a diffusion material for, for example, a diffusion sheet or diffusion panel for use in, for example, the lighting unit (backlight unit) of a liquid crystal display device; or a diffusion material for use, for example, in a member (screen) for forming an image with an image signal from a projector or in any one of various lighting units.

In addition, the method of blending fine particles in a diffusion material of the present invention enables the blending amounts of fine particles in a matrix to be designed so that a chromaticity variation of emitted light outgoing from a diffusion material with respect to incident light entering the diffusion material falls within a predetermined range, and can provide a diffusion material capable of emitting illumination light free from wavelength unevenness. Accordingly, the method can be utilized as a method of blending fine particles in: a diffusion material for, for example, a diffusion sheet or diffusion panel for use in, for example, the lighting unit (backlight unit) of a liquid crystal display device; or a diffusion material for use, for example, in a member (screen) for forming an image with an image signal from a projector or in any one of various lighting units.

In addition, the method of producing a diffusion material of the present invention enables the blending amounts of fine particles in a matrix to be designed so that a chromaticity variation of the emitted light outgoing from a diffusion material with respect to the incident light entering the diffusion material falls within a predetermined range, and enables a diffusion material capable of emitting illumination light free from wavelength unevenness to be produced. Accordingly, the method can be utilized as a method of producing: a diffusion material for, for example, a diffusion sheet or diffusion panel for use in, for example, the lighting unit (backlight unit) of a liquid crystal display device; or a diffusion material for use, for example, in a member (screen) for forming an image with an image signal from a projector or in any one of various lighting units.

The invention claimed is:

1. A diffusion material comprising:
   a matrix having a refractive index; and
   multiple kinds of fine particles, each kind of which has another refractive index different from said refractive index of said matrix, dispersed in said matrix in accordance with blending amounts,
   said blending amounts of said multiple kinds of fine particles being determined by
   determining a light intensity attenuating rate $C(\lambda)$ in said diffusion material so that chromaticity variations $\Delta x$ and $\Delta y$ of emitted light outgoing from said diffusion material with respect to incident light entering said diffusion material satisfy the following expression (9), respectively, $-0.03 \leq \Delta x \leq 0.03$ $-0.03 \leq \Delta y \leq 0.03$ \hfill (9);

determining a total cross-sectional area of scattering $S_{total}(\lambda)$ in said diffusion material at a wavelength $\lambda$ of said incident light entering said diffusion material so that a condition for said light intensity attenuating rate $C(\lambda)$ in said diffusion material thus determined is satisfied; and
   determining said blending amounts of said multiple kinds of fine particles dispersed in said matrix so that said total cross-sectional area of scattering $S_{total}(\lambda)$ in said diffusion material thus determined is determined as a total of cross-sectional areas of scattering $S(\lambda)$ of respective fine particles that are determined by Mie theory for all of said multiple kinds of fine particles dispersed in said matrix.

2. The diffusion material according to claim 1, wherein said total cross-sectional area of scattering $S_{total}(\lambda)$ in said diffusion material is determined by:

determining a relative refractive index $m_i$ between an i-th kind (i=2, ..., n) of fine particles and said matrix from the following expression (1); and determining said total cross-sectional area of scattering $S_{total}(\lambda)$ in said diffusion material from the following expressions (2-1) and (2) by using said relative refractive index $m_i$ thus determined:

$$m_i = n_{pi}(\lambda)/n_m(\lambda) \qquad (1)$$

$$S_r(\lambda) = N \sum_{i=1}^{\infty} S_i(m_i, \lambda) F(r_i) \qquad (2\text{-}1)$$

$$S_{total}(\lambda) = \sum_{i=1}^{n} S_i(\lambda) NA_i \quad \sum_{i=1}^{n} A_i = 1 \qquad (2)$$

where $n_m(\lambda)$ denotes said refractive index of said matrix, $n_{pi}(\lambda)$ denotes a refractive index of said i-th kind of fine particles, $A_i$ denotes a blending ratio at which said i-th kind of fine particles are blended, $r_i$ denotes a particle size of said i-th kind of fine particles, $F(r_i)$ denotes a particle size distribution function of said multiple kinds of fine particles, $m_i$ denotes said relative refractive index between said i-th kind of fine particles and said matrix, $S_i(m_i, \lambda)$ denotes cross-sectional areas of scattering of said i-th kind of fine particles, L denotes a thickness of said diffusion material, and N denotes a number density of fine particles in said diffusion material.

3. The diffusion material according to claim 2, wherein said particle size distribution function $F(r)$ of said fine particles is represented by the following expression (8):

$$F(r) = \frac{1}{\sqrt{2\pi Npq}} \exp\left[-\frac{(r-Np)^2}{2Npq}\right], q = 1-p \qquad (8)$$

where $N_0$ represents a total number of particles, $F(r)$ denotes the number of particles having a particle diameter of r, p denotes a probability that the particles having the particle diameter of r is present, Np denotes an average particle diameter, and Npq denotes a variance.

4. The diffusion material according to claim 1, wherein said total cross-sectional area of scattering $S_{total}(\lambda)$ in said diffusion material is determined by:

determining a relative refractive index $m_i$ between an i-th kind (i=2, ..., n) of fine particles and said matrix from the following expression (1); and determining said total cross-sectional area of scattering $S_{total}(\lambda)$ in said diffusion material from the following expressions (2-2) and (2) by using said relative refractive index $m_i$ thus determined:

$$m_i = n_{pi}(\lambda)/n_m(\lambda) \qquad (1)$$

$$S_i(\lambda) = N \sum_{0}^{\infty} S_i(\delta, m_i, \lambda) f_i(\delta) d\delta \qquad (2\text{-}2)$$

$$S_{total}(\lambda) = \sum_{i=1}^{n} S_i(\lambda) NA_i \quad \sum_{i=1}^{n} A_i = 1 \qquad (2)$$

where $n_m(\lambda)$ denotes said refractive index of said matrix, $n_{pi}(\lambda)$ denotes a refractive index of said i-th kind of fine particles, $A_i$ denotes a blending ratio at which said i-th kind of fine particles are blended, $\delta$ denotes a particle size of each of said fine particles, $f_i(\delta)$ denotes a particle size distribution function of said i-th kind of fine particles, $m_i$ denotes said relative refractive index between said i-th kind of fine particles and said matrix, $S_i(\delta, m_i, \lambda)$ denotes cross-sectional areas of scattering of said i-th kind of fine particles, L denotes a thickness of the diffusion material, and N denotes a number density of fine particles in said diffusion material.

5. The diffusion material according to claim 4, wherein a particle size distribution of said fine particles forms a normal distribution; and said particle size distribution function $f_i(\delta)$ is represented by the following expression (8-1):

$$f_i(\delta) = \frac{1}{\sigma_i \sqrt{2\pi}} \exp\left[-\frac{1}{2}\left(\frac{\delta - \mu_i}{\sigma_i}\right)^2\right] \qquad (8\text{-}1)$$

where $\mu_i$ denotes an average particle diameter of said i-th kind of fine particles, and $\sigma_i$ denotes a standard deviation of thereof.

6. The diffusion material according to claim 1, wherein said chromaticity variations $\Delta x$ and $\Delta y$ are determined by:

determining said light intensity attenuating rate $C(\lambda)$ in said diffusion material from the following expression (3) by using said total cross-sectional area of scattering $S_{total}(\lambda)$ in said diffusion material;

determining an intensity $P'(\lambda)$ of said emitted light outgoing from said diffusion material from the following expression (4) by using the thus determined light intensity attenuating rate $C(\lambda)$ and an intensity $P'(\lambda)$ of said incident light entering said diffusion material;

determining chromaticities x and y of said incident light, and chromaticities x' and y' of said emitted light from the following expressions (5) and (6) by using the thus determined intensity $P'(\lambda)$ of said emitted light and said intensity $P'(\lambda)$ of said incident light; and determining said chromaticity variations $\Delta x$ and $\Delta y$ of said emitted light with respect to said incident light from the following expression (7) by using the thus determined chromaticities x and y of said incident light, and the thus determined chromaticities x' and y' of said emitted light:

$$C(\lambda) = \exp[-S_{total}(\lambda) \cdot L] \qquad (3)$$

$$P'(\lambda) = C(\lambda) P(\lambda) \qquad (4)$$

-continued $$\begin{cases} X' = \int_\lambda P'(\lambda)\bar{x}(\lambda)d\lambda \\ Y' = \int_\lambda P'(\lambda)\bar{y}(\lambda)d\lambda \\ Z' = \int_\lambda P'(\lambda)\bar{z}(\lambda)d\lambda \end{cases} \begin{cases} X = \int_\lambda P(\lambda)\bar{x}(\lambda)d\lambda \\ Y = \int_\lambda P(\lambda)\bar{y}(\lambda)d\lambda \\ Z = \int_\lambda P(\lambda)\bar{z}(\lambda)d\lambda \end{cases} \quad (5)$$

where X', Y', and Z' denote tristimulus values of said emitted light, X, Y, and Z denote tristimulus values of said incident light, and xbar, ybar, and zbar denote color matching functions $$\begin{cases} x' = \dfrac{X'}{X'+Y'+Z'} \\ y' = \dfrac{Y'}{X'+Y'+Z'} \end{cases} \begin{cases} x = \dfrac{X}{X+Y+Z} \\ y = \dfrac{Y}{X+Y+Z} \end{cases} \quad (6)$$

$$\Delta x = x' - x \quad (7)$$
$$\Delta x = y' - y.$$

* * * * *